United States Patent
English et al.

(10) Patent No.: US 11,242,491 B2
(45) Date of Patent: Feb. 8, 2022

(54) CALCIUM REMOVAL OPTIMISATION

(71) Applicant: BP Corporation North America Inc., Houston, TX (US)

(72) Inventors: Jason English, Aurora, IL (US); Craig Hackett, Phoenix, AZ (US)

(73) Assignee: BP Corporation North America Inc., Houston, TX (US)

( * ) Notice: Subject to any disclaimer, the term of this patent is extended or adjusted under 35 U.S.C. 154(b) by 23 days.

(21) Appl. No.: 16/624,898

(22) PCT Filed: Jun. 6, 2018

(86) PCT No.: PCT/US2018/036199
§ 371 (c)(1),
(2) Date: Dec. 19, 2019

(87) PCT Pub. No.: WO2018/236580
PCT Pub. Date: Dec. 27, 2018

(65) Prior Publication Data
US 2020/0131442 A1  Apr. 30, 2020

Related U.S. Application Data

(60) Provisional application No. 62/521,631, filed on Jun. 19, 2017.

(51) Int. Cl.
| | | |
|---|---|---|
| *C10G 31/08* | (2006.01) | |
| *C10G 17/04* | (2006.01) | |
| *C10G 33/02* | (2006.01) | |
| *G01N 23/223* | (2006.01) | |
| *G01N 33/24* | (2006.01) | |

(52) U.S. Cl.
CPC ............ *C10G 31/08* (2013.01); *C10G 17/04* (2013.01); *C10G 33/02* (2013.01); *G01N 23/223* (2013.01); *G01N 33/241* (2013.01); *G01N 2223/076* (2013.01); *G01N 2223/637* (2013.01); *G01N 2223/652* (2013.01)

(58) Field of Classification Search
None
See application file for complete search history.

(56) References Cited

U.S. PATENT DOCUMENTS

| | | |
|---|---|---|
| 4,778,589 A | 10/1988 | Reynolds |
| 5,078,858 A | 1/1992 | Hart et al. |
| 5,660,717 A | 8/1997 | Lindemuth |
| 6,030,523 A | 2/2000 | Varadaraj et al. |
| 7,927,479 B2 | 4/2011 | Greaney et al. |
| 2004/0045875 A1 | 3/2004 | Nguyen et al. |
| 2011/0098082 A1 | 4/2011 | Kent et al. |
| 2011/0100877 A1 | 5/2011 | Snawerdt |
| 2011/0120913 A1 | 5/2011 | Snawerdt |
| 2012/0053861 A1 | 3/2012 | Kremer et al. |
| 2013/0168294 A1 | 7/2013 | Chakrabarty et al. |
| 2014/0198898 A1 | 7/2014 | Beumer et al. |

FOREIGN PATENT DOCUMENTS

| | | |
|---|---|---|
| CN | 1760340 A | 4/2006 |
| CN | 103797358 A | 5/2014 |
| CN | 104603242 A | 3/2017 |
| WO | 2008/062433 A2 | 5/2008 |

OTHER PUBLICATIONS

International Search Report for PCT/US2018/036199, dated Aug. 17, 2018.
Written Opinion of the International Searching Authority for PCT/US2018/036199, dated Dec. 27, 2018.

*Primary Examiner* — Tam M Nguyen
(74) *Attorney, Agent, or Firm* — McDonnell, Boehnen, Hulbert & Berghoff LLP

(57) ABSTRACT

A process for optimising the removal of calcium from a hydrocarbon feedstock in a refinery desalting process, the refinery desalting process comprising the following steps: (a) mixing one or more wash water streams with one or more hydrocarbon feedstock streams; (b) at least partially separating the wash water from the hydrocarbons in a refinery desalter; and (c) removing the separated water and hydrocarbons from the refinery desalter as one or more desalted hydrocarbon streams and one or more effluent water streams; the process optimisation comprising: (i) providing at least one x-ray fluorescence analyser at at least one point in the refinery desalting process; (ii) measuring the concentration of calcium at the at least one point in the process using the at least one x-ray fluorescence analyser; and (iii) optionally adjusting at least one process condition of the refinery desalting process in response to the calcium concentration measurement in step (ii). An apparatus comprises a desalter; a line through which one or more hydrocarbon feedstock streams are passed to the desalter; optionally a line through which one or more wash water streams are passed to the desalter; and one or more x-ray fluorescence analysers configured so as to measure the concentration of calcium in water or hydrocarbons at one or more positions within the apparatus.

19 Claims, No Drawings

CALCIUM REMOVAL OPTIMISATION

This application is a national stage application under 35 U.S.C. § 371 of International Application No. PCT/US2018/036199, filed Jun. 6, 2018, which claims priority to U.S. Provisional Application No. 62/521,631, filed Jun. 19, 2017, the disclosures of which are explicitly incorporated by reference herein.

FIELD OF THE INVENTION

The invention relates to the desalting of and removal of calcium from a hydrocarbon feedstock, such as crude oil. In particular, the invention relates to a process and apparatus for optimisation of the removal of calcium from a hydrocarbon feedstock such as crude oil during a refinery desalting operation.

BACKGROUND OF THE INVENTION

When crude oil is extracted from a reservoir, it contains water and salts. At the high temperatures that may be encountered in a refinery during crude oil processing, the water can hydrolyse the salts to form corrosive acids. Chloride salts are typically found in crude oil and pose a particular problem, since they can form hydrochloric acid. Bromide salts can also be found, and they can form hydrobromic acid.

Over time, corrosive acids can cause significant damage to refinery equipment. Damage is commonly observed in the lines that transport crude oil from one area of a refinery to another. Considerable time and cost may be involved in replacing damaged refinery equipment. In some cases, for instance where a bypass pipe has not been provided, processing of the crude oil will need to be stopped entirely in order for the refinery equipment to be replaced.

It is therefore desirable for salts to be removed from hydrocarbon fluids such as crude oil before refinery processing. To solve this problem, crude oils are typically passed to a desalter before they are processed in a refinery.

Crude oils are typically mixed with wash water before they are passed to a desalter. Once introduced into the desalter, a desalted crude oil phase and an aqueous phase form. The aqueous phase contains water (that which was present in the extracted crude oil, as well as water that has been added to the hydrocarbon stream during processing, such as wash water) and salt. A rag layer separates the two phases. The rag layer is a mixture of the aqueous phase and the desalted crude oil phase.

A desalted crude oil stream and an aqueous stream are withdrawn from the desalter through separate lines. The streams are typically withdrawn at points in the desalter which are a distance from the rag layer so as to minimize the presence of any aqueous components in the desalted crude oil stream and vice versa.

Methods are known for optimizing desalting processes. For instance, demulsifiers are often added to minimize the rag layer and encourage the formation of separate hydrocarbon and aqueous phases. The application of an electrostatic field to the desalting unit may also be used to encourage the formation of separate phases.

A hydrocarbon feedstock such as crude oil may also contain calcium. Typically, the calcium is present in the crude oil in the form of a calcium salt such as calcium chloride, calcium carbonate, calcium bicarbonate, calcium phosphate, calcium phenolate, or calcium naphthenates. Calcium in crude oil can cause significant issues such as fouling, catalyst poisoning and poor coke quality. In order to allow processing of crudes containing high amounts of calcium, oil refineries must either blend high calcium crudes with lower calcium crudes before processing, or must take steps to remove the calcium before processing. Calcium removal has become an important concern over the last few years due to increasing use of crudes with very high levels of calcium (such as some from the African continent that contain over 200 ppm, and some nearly 400 ppm of calcium).

Calcium removal in oil refineries is typically carried out in the refinery desalter during the desalting operation. Processes for removing the calcium from the crude oil include adding an acid, application of a solids wetter, application of a reverse breaker, or addition of a calcium scale inhibitor.

The use of acids and other additives in calcium removal processes presents challenges that require close monitoring and optimization in order to maximize the calcium removal from the crude blend without leading to negative impacts such as those due to acid carryover into the crude. Over acidification may also cause a reduced rate of coalescence, higher crude conductivities which can negatively impact the ability of an electric field to coalesce water droplets in the crude during the desalting operation, and corrosion of the desalter apparatus due to the acidic pH.

Various attempts in the art have been made to monitor and optimise desalting operations.

U.S. Pat. No. 7,927,479 discloses online monitoring of particle size and counts during a desalting operation using focused beam reflectance. There is no mention of calcium removal or the monitoring of calcium concentration.

US2011/0100877 discloses methods of removing calcium from crude oil in a refinery desalting operation by adding an acid additive to the desalter. The process involves measuring at least one process characteristic; performing a statistical calculation of the desalting process performance based upon the measuring; and adjusting a control setting of the desalting process as a function of the statistical calculation.

US2011/0098082 discloses methods for removing calcium and other metals from crude oil during a refinery desalting process where an acid additive is introduced to the desalter. The process comprises measuring a concentration of the metal in the oil or aqueous phase and altering a characteristic of the desalting process to maintain residual impurity levels within the desalted crude as a function of the measured concentration.

US2011/0120913 discloses a method for removing calcium and other metals from crude oil in a refinery desalting process where an acid additive is introduced to the desalter. The process involves running a plurality of tests to determine at least one statistically significant processing characteristic of the refinery desalting process and adjusting a control setting of the processing characteristic as a function of the tests.

The measurement steps of US2011/0100877, US2011/0098082 and US2011/0120913 involve transfer of samples of the fluid within the desalter to measurement stations where statistical calculations are carried out to provide information about the desalting process. These documents disclose what is known in the art to be "off-line" monitoring of calcium concentration. The processes involve collecting a sample of fluid from the desalter before analysing and testing the sample to determine properties of the fluid such as calcium concentration. Such monitoring only gives an indication of the calcium concentration of that specific sample at the specific time of measurement. If, on the basis of the measurement, the process operator wants to adjust a process condition, by the time the sample measurement is done and the process operator has the requisite information to make an adjustment decision, the sample measurement may no longer be representative of what is going on within the desalter. In this respect, the process operator is constantly "behind schedule" in monitoring the calcium removal process. Such off-line measurement techniques also have disadvantages associated with them such as the process of sample collecting being inefficient and time consuming. Furthermore, with off-line monitoring, it is difficult to get a sample that is truly representative of calcium concentration and what is going on in the desalter.

US2012/0053861 discloses methods of estimating the onset of corrosive species formation in an overhead fluid system along a process stream from the value of a variety of measured parameters of the fluid.

US2014/0198898 discloses using X-ray fluorescence (XRF) analysers in the on-line measurement of process parameters in refinery processes and subsequent optimisation of said processes.

The inventors of the present invention have appreciated that there exists a need for further optimisation of processes for calcium removal during desalting operations. One of the challenges for running a calcium removal program is having ready access to calcium data to gauge the effectiveness of a program. The inventors have appreciated that there exists a need for real-time monitoring of process parameters in a calcium removal operation. This would enable a sufficient amount of process data to be obtained in real-time and allow the process conditions to be adjusted so as to provide optimisation of the calcium removal process. This is contrasted to existing processes in the art where measurement of process parameters is done by taking samples of the fluid from the refinery desalter before each sample is analysed. Sometimes, it may take a significant amount of time to analyse each sample or to analyse a significant enough quantity of samples before enough information is obtained to make a decision on adjusting process parameters. By this stage, disadvantages that may occur from not adjusting the process conditions in an appropriate time frame may already have occurred. The inventors have further appreciated that there is a need to identify the particular process parameters to be monitored that would provide the most effective optimisation of calcium removal processes, and also to identify the specific points in a process chain where measurement of a particular parameter or combination of parameters can provide the most information for optimisation of the calcium removal. The inventors have further appreciated the need to optimise calcium removal operations by identifying what specific adjustments can be made to specific process conditions from the measured data in order to effectively optimise the process.

SUMMARY OF THE INVENTION

According to an aspect of the invention, there is provided a process for optimising the removal of calcium from a hydrocarbon feedstock in a refinery desalting process, wherein the refinery desalting process comprises the following steps:
(a) mixing one or more wash water streams with one or more hydrocarbon feedstock streams;
(b) at least partially separating the wash water from the hydrocarbons in a refinery desalter; and
(c) removing the separated water and hydrocarbons from the refinery desalter as one or more desalted hydrocarbon streams and one or more effluent water streams;

wherein the process optimisation comprises:
(i) providing at least one x-ray fluorescence analyser at at least one point in the refinery desalting process;
(ii) measuring the concentration of calcium at the at least one point in the process using the at least one x-ray fluorescence analyser; and
(iii) optionally adjusting at least one process condition of the refinery desalting process in response to the calcium concentration measurement in step (ii).

According to another aspect of the invention, there is provided an apparatus comprising:
a desalter;
a line through which one or more hydrocarbon feedstock streams are passed to the desalter;
optionally a line through which one or more wash water streams are passed to the desalter; and
one or more x-ray fluorescence analysers configured so as to measure the concentration of calcium in water or hydrocarbons at one or more positions within the apparatus.

According to another aspect of the invention, there is provided the use of one or more-ray fluorescence analysers for optimising calcium removal in a refinery desalting process in which one or more hydrocarbon feedstock streams are desalted so as to produce one or more desalted hydrocarbon streams.

In all aspects of the invention, preferably, the process comprises on-line measurement of the calcium concentration at at least one point in the process.

DETAILED DESCRIPTION OF THE INVENTION

The present invention is based on the finding that calcium removal in refinery desalting operations can be optimised by measuring the calcium concentration at at least one point in the process. It has been found that the calcium concentration can be monitored in real-time by at least one x-ray fluorescence (XRF) analyser so to provide on-line measurement of calcium concentration in the process stream at one or more points in the process. Calcium concentration measurements can optionally be combined with measurements of further parameters (using XRF analysers or other apparatus) in order to provide real-time data of the calcium removal process as it is happening. This data can be used to determine an adjustment that needs to be made to one or more process conditions of the calcium removal process in order to effectively optimise the process of calcium removal. This adjustment of one or more process conditions can occur automatically as the calcium data is fed to a computer which can make a decision on the adjustment of one or more process conditions on the basis of the measured data. Alternatively, the process condition adjustment can be made manually by a process operator on the basis of the measured data.

The general process of refinery desalting operations is known in the art and the skilled person will be familiar with such operations. Typically, one or more hydrocarbon feedstock streams are mixed with one or more wash water streams. This mixture is then introduced into a refinery desalter. The one or more wash water streams may be mixed with the one or more hydrocarbon feedstock streams prior to introduction to the desalter. Alternatively, the one or more wash water streams can be introduced to the refinery desalter separately to the one or more hydrocarbon feedstock streams such that the water and hydrocarbons do not mix until present in the desalter. Upon mixing, the one or more wash water streams and the one or more hydrocarbon feedstock streams typically form an emulsion, although this is not essential. The emulsion is generally a water-in-oil emulsion. If the hydrocarbon feedstock and wash water separate or partially separate, a rag layer may exist between the two phases that comprises both wash water and hydrocarbons.

During the desalting process, typically, salts present in the hydrocarbon feedstock (either present directly within the hydrocarbon feedstock or present within residual water present in the hydrocarbon feedstock) migrate into the wash water phase. The hydrocarbons and water are then removed from the refinery desalter as one or more desalted hydrocarbon streams and one or more effluent water streams after the hydrocarbons and water within the desalter at least partially separate. Within the refinery desalter, the desalting process may comprise applying an electric field to the mixture of water and hydrocarbons. This may cause dispersed droplets of water and oil to coalesce such that the hydrocarbons and water begin to form distinct separated phases. This may aid in separation of the water from the hydrocarbons. The desalting process may also typically comprise subjecting the mixture of water and hydrocarbons in the refinery desalter to temperature. For example, a desalting process may comprise heating the mixture of water and hydrocarbons in the desalter to a temperature of from 100° C. to 150° C.

Any conventional desalter design may be used in the invention. A desalter will typically have one or more inlets for the one or more hydrocarbon feedstock streams, one or more wash water streams, or streams that comprise a mixture of wash water and hydrocarbon feedstock. The desalter will generally also comprise a hydrocarbon outlet and an aqueous outlet. In the process of the invention, the hydrocarbon feedstock and wash water may typically be introduced into the desalter via a feedstock inlet. A desalted hydrocarbon stream is removed from the desalter via the hydrocarbon outlet. An aqueous phase is removed from the desalter via the aqueous outlet. Typically, where a mixture of the hydrocarbon feedstock and wash water are introduced to the refinery desalter, a mixing valve may be included in a line that introduces the mixture of hydrocarbons and water to the desalter so as to effectively mix the water and hydrocarbons prior to introduction to the desalter. The hydrocarbon feedstock is typically passed to the desalter in an amount of from 100-100,000 barrels per hour, preferably from 500-50,000 barrels per hour, more preferably from 1,000-20,000 barrels per hour.

The hydrocarbon feedstock may be any refinery feedstock. The hydrocarbon feedstock may be selected from a crude oil, a synthetic crude, a biocomponent, an intermediate stream such as a residue, gas oil, vacuum gas oil, naphtha and cracked stocked, and blends thereof. For instance, a blend of one or more crude oils or a blend of one or more crude oils with a synthetic crude may be used. Typically, the hydrocarbon feedstock will comprise a crude oil.

The hydrocarbon feedstock will typically comprise a small quantity of water. The water that is present in the hydrocarbon feedstock may be residual water that is present in the hydrocarbon feedstock. For instance, where the hydrocarbon feedstock comprises crude oil, brine may be present in the crude oil from extraction from a reservoir. Alternatively, residual water may be present in the hydrocarbon feedstock, for instance from a previous desalting process. Water will typically be present in the hydrocarbon feedstock in an amount of less than 10% by weight, less than 5%, such as around 3% by weight of the hydrocarbon feedstock. It will be appreciated that these amounts do not include further wash water that is typically added to the hydrocarbon feedstock along the line to the desalter.

The hydrocarbon feedstock also typically comprises a salt. The salt may be an inorganic salt. The salt may be selected from alkali and alkaline earth metal salts, such as alkali and alkaline earth metal halides. Typical salts which may be found in hydrocarbon feedstocks include sodium chloride, calcium chloride, potassium chloride and magnesium chloride. Crude oil typically contains sodium chloride. Potassium chloride and magnesium chloride may also be found in crude oil, though typically in smaller amounts than sodium chloride. The amount of salt that is present will vary between different hydrocarbon feedstocks. The hydrocarbon feedstock will typically contain one or more inorganic chlorides in a total amount of 1-300 ppm, such as 2-100 ppm.

Further components that are typically found in a refinery feedstock may also be present in the hydrocarbon feedstock. For instance, where the hydrocarbon feedstock comprises crude oil, asphaltenes will typically be present.

The one or more wash water streams are typically mixed with the hydrocarbon feedstock in an amount of 1-30%, preferably 3-20%, and more preferably 5-10% by weight of the hydrocarbon feedstock. In some instances, a plurality of wash water streams are mixed with the hydrocarbon feedstock. In these instances, the amounts referred to above relate to the total amount of wash water that is mixed with the total amount of hydrocarbon feedstock. The one or more wash water streams may comprise any suitable form of water such as fresh water, seawater, brine, or any combination thereof.

The refinery desalting process also comprises removing calcium from the hydrocarbon feedstock. Calcium is generally present in the hydrocarbon feedstock in the form of a calcium salt. The calcium salt may be any calcium salt normally found within hydrocarbon feedstocks such as crude oil. Examples of calcium salts typically found in hydrocarbon feedstock such as crude oil include calcium chloride, calcium carbonate, calcium bicarbonate, calcium phosphate, calcium phenolate, calcium naphthenates, or any combination thereof.

The calcium salts removed during the calcium removal process in the refinery desalter may be dissolved in the one or more hydrocarbon feedstock streams, dissolved in water residual in the one or more hydrocarbon feedstock streams, suspended within the one or more hydrocarbon feedstock streams, suspended within water residual in the one or more hydrocarbon feedstock streams, or any combination thereof.

The process of removing calcium from the hydrocarbon feedstock during the refinery desalting process may comprise the addition of one or more additives to the mixture of hydrocarbons and wash water in the refinery desalter. Additives can be added to the one or more hydrocarbon feedstock streams, one or more wash water streams, or mixture of hydrocarbon feedstock and water streams prior to the addition of said hydrocarbons and water to the refinery desalter. Alternatively, the one or more additives may be introduced directly into the desalter once the hydrocarbon feedstock and wash water are already present in the desalter.

The additives may comprise any suitable additive for removing calcium from the hydrocarbon feedstock and causing it to enter the aqueous phase present in the desalter. Preferably, the additives comprise one or more acids, one or more solids wetters, one or more reverse breakers, one or more calcium scale inhibitors or any combination thereof.

Examples of suitable acids for calcium removal include organic acids and inorganic acids. Examples of suitable organic acids include carboxylic acids, hydroxycarboxylic acids, functionalised polymers of acrylic acid, and combinations thereof. Examples of such specific compounds are known to the skilled person and can be found in numerous patents in the field such as U.S. Pat. Nos. 4,778,589, 5,078,858, 5,660,717 and US2004/0045875. The acid additives used in calcium removal are typically added to the hydrocarbons in an amount of from 10-1000 ppm in water.

Examples of suitable reverse breakers for calcium removal include cationic polymers. Examples of such cationic polymers include polyamine condensates, polyvinylamines, polyaminoacrylates, or combinations thereof. The reverse breakers are typically present in an amount of from 25-1000 ppm in water.

Examples of suitable solids wetters include sulfonated oils, ethoxylated castor oils, ethoxylated phenolformaldehyde resins, polyether materials, polyester materials, or any combination thereof. The solids wetters are typically present in an amount of from 2-100 ppm in water.

Examples of suitable calcium scale inhibitors include phosphonobutane-1,2,4-tricarboxylic acid (PBTC), aminotrimethylene phosphonic acid (ATMP) 1-hydroxyethylidene-1,1-diphosphonic acid (HEDP), polyacrylic acid (PAA), a phosphinopolyacrylate, a polymaleic acid (PMA), a maleic acid terpolymer (MAT), a sulfonic acid copolymer, or any combination thereof. The calcium scale inhibitors are typically present in an amount of from 5-100 ppm in water.

The process of the invention comprises providing at least one x-ray fluorescence analyser at at least one point in the refinery desalting process. The at least one x-ray fluorescence analyser can be any suitable type of x-ray fluorescence analyser for measuring the concentration of calcium in hydrocarbons, water, or a mixture of hydrocarbons and water. Typically, the at least one x-ray fluorescence analyser comprises a monochromatic optic enabled XRF analyser. Typically, the at least one x-ray fluorescence analyser focuses energy to or from the one or more hydrocarbon feedstock streams, the one or more desalted hydrocarbon streams, the one or more wash water streams, the one or more effluent water streams, the mixture of hydrocarbons and water in the desalter or prior to the desalter, or any combination thereof using an X-ray engine having at least one focusing, monochromatic x-ray optic.

The at least one x-ray fluorescence analyser may comprise a window separating the x-ray engine from the one or more hydrocarbon feedstock streams, the one or more desalted hydrocarbon streams, the one or more wash water streams, the one or more effluent water streams, the mixture of hydrocarbons and water in the desalter or prior to the desalter, or any combination thereof.

The at least one x-ray fluorescence analyser may comprise a Monochromatic Wavelength Dispersive X-ray fluorescence (MWDXRF) analyser or a Monochromatic Excitation, Energy Dispersive X-ray fluorescence (ME-EDXRF) analyser, or any combination thereof.

Examples of such x-ray fluorescence analysers that may be used in the process and apparatus of the present invention include those disclosed in US2014/0198898, although other x-ray analysers known in the art may also be used.

The process of the present invention optionally comprises a step of adjusting at least one process condition of the refinery desalting process in response to the calcium concentration measurement performed in step (ii) of the process of the invention. Preferably, the process of the invention comprises such a step.

The step of adjusting at least one process condition of the refinery desalting process in response to the calcium concentration measurement performed in step (ii) may be carried out automatically. For example a computer programme configured to receive data of the measurements carried out in step (ii) may automatically adjust a process condition in response to the calcium concentration measurement of step (ii). Alternatively, the step of adjusting at least one process condition of the refinery desalting process in response to the calcium concentration measurement performed in step (ii) may be carried out manually by an operator monitoring the data of the calcium concentration measurements from step (ii). In this embodiment, on inspection and optional analysis of the measurement data from step (ii), the operator may adjust a process condition of the refinery desalting process so as to optimise the process.

Step (ii) of measuring the concentration of calcium at the at least one point in the process using the at least one x-ray fluorescence analyser preferably comprises on-line measurement of the calcium concentration. The term on-line measurement as used herein is a term of art, and is typically used to refer to measurement of a parameter, for example, calcium concentration as the process is occurring. In on-line measurement, the measurement data is produced in a short time frame (for example straight away, or in a few seconds or minutes) such that the process operator (whether a person or computer) has access to the data as the process is still going on. Typically, on-line monitoring involves the measuring of one or more process parameters at a constant rate, with relatively short time intervals between each measurement. This allows a change in the one or more process parameters to be determined in real-time as the process is going on. The operator may then make a decision with regard to the process on the basis of the data whilst the process is still going on such that any necessary adjustments required to optimise the process can be made straightaway. In this respect, on-line measurement provides real-time monitoring of the process and can lead to optimisations and increased efficiencies of a process. This is contrasted to monitoring that is not on-line. For example, where a sample of fluid is collected from a process stream and analysed away from the process stream. Such an analysis may take a significant amount of time (such as several hours, days or weeks) to generate measurement data regarding the process. This may mean that any inefficiencies that exist in the process, and adjustments that may be required in order to optimise the process are not determined until the process is complete or at least until a later stage in the process. This could mean that any process adjustments necessary to optimise the process are not realised until too late. In a preferable embodiment, all calcium concentration measurements are done by on-line measurement.

The process optimisation of the present invention may comprise the measurement of one or more additional process parameters or conditions in addition to the measured calcium concentration. These additional one or more process parameters can be measured by x-ray fluorescence analysers. Alternatively, the one or more additional process parameters can be measured by other suitable means known in the art. Preferably, the one or more additional process parameters are also monitored by on-line measurement, although this is not essential. Most preferably, both the calcium concentration and one or more additional process parameters are measured by on-line measurement. In a preferable embodiment, all calcium concentration measurements and all measurements of the one or more additional process parameters are done by on-line measurements.

Step (ii) of measuring the concentration of calcium at the at least one point in the process using the at least one x-ray fluorescence analyser and/or the optional step of measuring at least one additional process parameter may comprise both on-line measurements and laboratory measurements.

The inventors of the present invention have appreciated that in order to optimise calcium removal during refinery desalting processes, there is a need to identify the specific process parameters that when measured would provide for the most effective process optimisation. For example, there is a need to identify what specific parameters and specific combinations of parameters that when measured would provide sufficient information regarding the ongoing desalting process to enable a process operator or computer to make a decision on the basis of the measured data with regard to an adjustment of the process that would provide for its effective optimisation.

It has been found that measuring calcium concentration, preferably by on-line measurement is a particularly useful parameter to monitor for calcium removal in refinery desalting operations. The on-line measurement of calcium concentration in real-time has been found to provide sufficient data for a process operator to make adjustments to the desalting process as it is going on such that the process can be optimised.

The calcium concentration can be measured at any suitable point in the desalting process stream. For example, the step of measuring the concentration of calcium at the at least one point in the process using the at least one x-ray fluorescence analyser may comprise measuring calcium concentration of the one or more hydrocarbon feedstock streams prior to introduction to the desalter, measuring calcium concentration in the one or more desalted hydrocarbon streams after the desalter, measuring calcium concentration in the one or more wash water streams prior to introduction to the desalter, measuring calcium concentration in the one or more effluent water streams after the desalter, measuring calcium concentration of a mixture of hydrocarbons and water in the desalter, measuring calcium concentration of a separated aqueous phase and/or separated hydrocarbon phase present in the desalter, or any combination thereof.

The process optimisation of the invention may comprise measuring at least one additional process parameter in addition to the calcium concentration. The inventors have appreciated that the identification of specific additional process parameters and combinations of process parameters to be measured is important in effectively optimising the process of calcium removal in a refinery desalter. Specifically, there is a need to identify those combinations of process parameters that when measured provide the most useful data for optimisation of the process for a process operator and enable a decision on adjustment of the process to be made on the basis of the data in order to optimise the process.

It has been found that the following additional process parameters are useful to measure in addition to the calcium concentration in order to provide sufficient data to provide for the most effective process optimisation: pH, iron content, ammonia concentration, amine concentration, or combinations thereof. Monitoring of the Ca concentration in combination with amines and/or ammonia is particularly preferred.

Preferably, the process of the invention comprises monitoring pH at at least one point in the desalting process stream in addition to the calcium concentration. Measuring the pH at at least one point in the desalting process stream may comprise measuring the pH at any point found suitable for providing data that may be used to make a decision with regard to a process adjustment that may optimise the calcium removal. Measuring the pH may typically comprise measurement of the pH of the one or more wash water streams, the one or more effluent water streams, the water present in the desalter, or any combination thereof. Where the process of the invention comprises the addition of one or more acids to at least one point in the desalting process, the process preferably comprises the measurement of pH at at least one point in the desalting process stream.

It has been found that a combination of calcium concentration measurement and pH measurement at at least one point in the desalting process stream is particularly useful for optimising the process of calcium removal. Measuring calcium concentration on-line in combination with pH has been found to provide sufficient data for a process operator or computer to make an informed decision with regard to control of the process so as to effectively optimise the process. The decision may comprise making an adjustment to at least one condition of the desalting process.

In some instances, step (ii) of measuring the concentration of calcium at the at least one point in the process using the at least one x-ray fluorescence analyser comprises measurement of calcium concentration in the one or more desalted hydrocarbon streams and measurement of the pH of the one or more effluent water streams. In this instance, step (iii) of optionally adjusting at least one process condition of the refinery desalting process in response to the calcium concentration measurement in step (ii) may comprise adjusting the rate of addition of one or more acids to the desalting process stream.

In some instances, step (ii) of measuring the concentration of calcium at the at least one point in the process using the at least one x-ray fluorescence analyser comprises measurement of calcium concentration in the one or more hydrocarbon feedstock streams and the one or more desalted hydrocarbon streams. Calcium concentration measurement at these locations allows for a determination of the calcium removal efficiency of the process. Since the calcium concentration in the hydrocarbons both prior to and after the desalting process is measured, the extent to which the process has removed calcium from the hydrocarbons is determined. In this instance, step (ii) may optionally comprise measuring the pH of the one or more effluent water streams. In this instance, step (iii) of optionally adjusting at least one process condition of the refinery desalting process in response to the calcium concentration measurement in step (ii) may comprise adjusting the rate of addition of one or more acids to the desalting process stream.

In some instances, step (ii) of measuring the concentration of calcium at the at least one point in the process using the at least one x-ray fluorescence analyser comprises measurement of calcium concentration in the one or more hydrocarbon feedstock streams, the one or more desalted hydrocarbon streams, and the one or more effluent water streams. This instance allows for a complete calcium balance to be determined across the desalter.

Step (iii) of optionally adjusting at least one process condition of the refinery desalting process in response to the calcium concentration measurement in step (ii) may comprise any suitable adjustment to one or more process conditions. The adjustment may be done by an operator of the process on inspection of the measurements from step (ii). Alternatively, the adjustment may be done automatically by a computer configured to receive and analyse the measurements of step (ii) on receipt and analysis of the measurements from step (ii).

Typically, step (iii) of optionally adjusting at least one process condition of the refinery desalting process comprises adjusting the rate of introduction of one or more acids to the process; the rate of introduction of one or more reverse breakers to the process; the rate of introduction of one or more solids wetters to the process; the rate of introduction of one or more calcium scale inhibitors to the process; temperature within the refinery desalter; pressure within the refinery desalter; the mix valve drop pressure; rate of introduction of the one or more hydrocarbon feedstock streams; rate of introduction of the one or more wash water streams; the strength of the electric field applied in the refinery desalter; the presence, absence, or amount of one or more additives in the wash water stream or hydrocarbon feedstock stream; the concentration of acid, solids wetter, reverse breaker, or calcium scale inhibitor if used; or any combination thereof.

In some instances, removing calcium from the hydrocarbons during the refinery desalting process comprises the step of adding at least one acid to the mixture of water and hydrocarbons, the one or more wash water streams, the one or more hydrocarbon feedstock streams, or any combination thereof; and step (iii) of adjusting at least one process condition of the refinery desalting process in response to the calcium concentration measurement in step (ii) comprises adjusting the rate of addition of the acid.

In some instances, removing calcium from the hydrocarbons during the refinery desalting process further comprises the step of adding a solids wetter to the mixture of water and hydrocarbons, the one or more wash water streams, the one or more hydrocarbon feedstock streams, or any combination thereof; and step (iii) of adjusting at least one process condition of the refinery desalting process in response to the calcium concentration measurement in step (ii) comprises adjusting the rate of introduction of the solids wetter.

In some instances, removing calcium from the hydrocarbons during the refinery desalting process further comprises the step of adding a reverse breaker to the mixture of water and hydrocarbons, the one or more wash water streams, the one or more hydrocarbon feedstock streams, or any combination thereof, and step (iii) of adjusting at least one process condition of the refinery desalting process in response to the calcium concentration measurement in step (ii) comprises adjusting the rate of introduction of the reverse breaker.

In some instances, removing calcium from the hydrocarbons during the refinery desalting process further comprises the step of adding a calcium scale inhibitor to the mixture of water and hydrocarbons, the one or more wash water streams, the one or more hydrocarbon feedstock streams, or any combination thereof; and step (iii) of adjusting at least one process condition of the refinery desalting process in response to the calcium concentration measurement in step (ii) comprises adjusting the rate of introduction of the calcium scale inhibitor.

The invention claimed is:

1. A process for optimising the removal of calcium from a hydrocarbon feedstock in a refinery desalting process, wherein the refinery desalting process comprises the following steps:
   (a) mixing one or more wash water streams with one or more hydrocarbon feedstock streams;
   (b) at least partially separating the wash water from the hydrocarbons in a refinery desalter; and
   (c) removing the separated water and hydrocarbons from the refinery desalter as one or more desalted hydrocarbon streams and one or more effluent water streams;
   wherein the process optimisation comprises:
   (i) providing at least one x-ray fluorescence analyser at at least one point in the refinery desalting process;
   (ii) measuring the concentration of calcium at the at least one point in the process using the at least one x-ray fluorescence analyser; and
   (iii) optionally adjusting at least one process condition of the refinery desalting process in response to the calcium concentration measurement in step (ii); and
   wherein the process optimisation further comprises measuring at least one additional process parameter selected from the pH of the one or more wash water streams, the pH of the one or more effluent water streams, the pH of the mixture of the water and hydrocarbons, the iron concentration at at least one point in the process, the amine concentration at at least one point in the process, and any combination thereof.

2. A process according to claim 1, wherein step (ii) comprises on-line measurement of the calcium concentration.

3. A process according to claim 1, wherein the step b) of at least partially separating the wash water from the hydrocarbons in a refinery desalter comprises applying an electric field to the water and the hydrocarbons present in the refinery desalter.

4. A process according to claim 1, wherein the hydrocarbon feedstock comprises sodium chloride, calcium chloride, magnesium chloride, or any combination thereof.

5. A process according to claim 1, wherein the one or more wash water streams and one or more hydrocarbon feedstock streams are mixed prior to being introduced into the refinery desalter or in the refinery desalter.

6. A process according to claim 1, wherein removing calcium from the hydrocarbons during the refinery desalting process comprises the step of adding an acid, a solids wetter, a reverse breaker, a calcium scale inhibitor or any combination thereof to the one or more wash water streams, the one or more hydrocarbon feedstock streams, the mixture of hydrocarbons and water, or any combination thereof.

7. A process according to claim 1, wherein the calcium is present in the hydrocarbon feedstock stream in the form of a calcium salt.

8. A process according to claim 7, wherein the calcium salt is dissolved in the one or more hydrocarbon feedstock streams, dissolved in water residual in the one or more hydrocarbon feedstock streams, suspended within the one or more hydrocarbon feedstock streams, suspended within water residual in the one or more hydrocarbon feedstock streams, or any combination thereof.

9. A process according to claim 1, wherein the measurement of the at least one additional process parameter comprises on-line measurement.

10. A process according to claim 1, wherein the removing calcium from the hydrocarbons during the refinery desalting process further comprises the step of adding at least one acid to the mixture of water and hydrocarbons, the one or more wash water streams, the one or more hydrocarbon feedstock streams, or any combination thereof; and wherein step (iii) of adjusting at least one process condition of the refinery desalting process in response to the calcium concentration measurement in step (ii) comprises adjusting the rate of addition of the acid.

11. A process according to claim 1, wherein the removing calcium from the hydrocarbons during the refinery desalting process further comprises the step of adding a calcium scale inhibitor to the mixture of water and hydrocarbons, the one or more wash water streams, the one or more hydrocarbon feedstock streams, or any combination thereof; and wherein step (iii) of adjusting at least one process condition of the refinery desalting process in response to the calcium concentration measurement in step (ii) comprises adjusting the rate of introduction of the calcium scale inhibitor.

12. A process according to claim 11, wherein the calcium scale inhibitor comprises phosphonobutane-1,2,4-tricarboxylic acid (PBTC), amino-trimethylene phosphonic acid (ATMP) 1-hydroxyethylidene-1,1-diphosphonic acid (HEDP), polyacrylic acid (PAA), a phosphinopolyacrylate, a polymaleic acid (PMA), a maleic acid terpolymer (MAT), a sulfonic acid copolymer, or any combination thereof.

13. A process according to claim 1, wherein step (ii) of measuring the concentration of calcium at the at least one point in the process using the at least one X-ray fluorescence analyser comprises measuring the concentration of calcium in the one or more desalted hydrocarbon streams or the one or more hydrocarbon feedstock streams, or both.

14. A process according to claim 13, wherein step (ii) of measuring the concentration of calcium at the at least one point in the process using the at least one X-ray fluorescence analyser comprises measuring the concentration of calcium in the one or more effluent water streams.

15. A process according to claim 13, wherein the process further comprises measuring the pH of the wash water stream, the pH of the effluent water stream, or both.

16. A process according to claim 13, wherein removing calcium from the hydrocarbons during the refinery desalting process further comprises the step of adding an acid, a solids wetter, a reverse breaker, a calcium scale inhibitor or any combination thereof to the one or more wash water streams, the one or more hydrocarbon feedstock streams, the mixture of water and hydrocarbons, or any combination thereof; and wherein the step (iii) of adjusting the at least one process condition of the refinery desalting process comprises adjusting the rate of introduction of the acid, the solids wetter, the reverse breaker, the calcium scale inhibitor or any combination thereof.

17. A process according to claim 1, wherein step (ii) of measuring the concentration of calcium at the at least one point in the process using the at least one x-ray fluorescence analyser and/or the optional step of measuring at least one additional process parameter comprises both on-line measurements and laboratory measurements.

18. A process according to claim 1, wherein step (iii) of optionally adjusting at least one process condition of the refinery desalting process in response to the calcium concentration measurement in step (ii) comprises adjusting any one or more of the following desalting process parameters: temperature within the refinery desalter; pressure within the refinery desalter; mix valve drop pressure; rate of introduction of the one or more hydrocarbon feedstock streams; rate of introduction of the one or more wash water streams; the strength of the electric field applied in the refinery desalter; the presence, absence, or amount of one or more additives in the wash water stream or hydrocarbon feedstock stream; the concentration of acid, solids wetter, or reverse breaker, or calcium scale inhibitor if used; or any combination thereof.

19. A process according to claim 1, wherein step (iii) of optionally adjusting at least one process condition of the refinery desalting process in response to the calcium concentration measurement in step (ii) comprises automatically adjusting the at least one process condition in response to the calcium concentration measurement in step (ii).

* * * * *